(12) United States Patent
Kanno

(10) Patent No.: US 7,703,414 B2
(45) Date of Patent: Apr. 27, 2010

(54) CHAMBER DEVICE, RESPIRATORY PHARMACOLOGICAL TEST SYSTEM AND PHARMACOLOGICAL SAFETY TEST METHOD

(75) Inventor: Akihiro Kanno, Higashimatsuyama (JP)

(73) Assignee: Drug Safety Testing Center Co., Ltd., Saitama (JP)

( * ) Notice: Subject to any disclaimer, the term of this patent is extended or adjusted under 35 U.S.C. 154(b) by 657 days.

(21) Appl. No.: 11/574,382

(22) PCT Filed: Aug. 1, 2005

(86) PCT No.: PCT/JP2005/014030

§ 371 (c)(1),
(2), (4) Date: Feb. 27, 2007

(87) PCT Pub. No.: WO2007/015289

PCT Pub. Date: Feb. 8, 2007

(65) Prior Publication Data

US 2007/0272166 A1  Nov. 29, 2007

(51) Int. Cl.
*A01K 1/00* (2006.01)
*A01K 1/02* (2006.01)
(52) U.S. Cl. .................. 119/418; 119/417; 119/496
(58) Field of Classification Search ......... 119/416–421, 119/480, 496, 452, 453, 677, 678; 137/255, 137/262, 576
See application file for complete search history.

(56) References Cited

U.S. PATENT DOCUMENTS

| | | | | |
|---|---|---|---|---|
| 3,877,420 | A * | 4/1975 | Eagleson Jr. ................ | 119/419 |
| 4,526,133 | A * | 7/1985 | LoMaglio .................... | 119/419 |
| 4,907,536 | A | 3/1990 | Chrisler | |
| 6,352,076 | B1 * | 3/2002 | French .................. | 128/203.12 |
| 6,723,055 | B2 | 4/2004 | Hoffman | |
| 7,234,269 | B2 * | 6/2007 | Yonker et al. .............. | 43/132.1 |
| 7,331,341 | B2 * | 2/2008 | Nelson .................. | 128/203.12 |
| 2005/0066908 | A1 | 3/2005 | Park | |

FOREIGN PATENT DOCUMENTS

JP  59-122949  7/1984
JP  2003319727 A  * 11/2003

OTHER PUBLICATIONS

English translation of International Preliminary Report on Patentability of PCT/JP2005/014030 issued by WIPO.

* cited by examiner

*Primary Examiner*—Kimberly S Smith
*Assistant Examiner*—Danielle Bates
(74) *Attorney, Agent, or Firm*—Sughrue Mion, PLLC

(57) ABSTRACT

The invention provides a system for respiratory pharmacology test and a chamber device that enables respiratory pharmacology test on particular large animals under unanesthetized, unrestrained state, with easy acclimatization and reduced effect of stress, and a method for conducting safety pharmacology studies on the same large animal individual. The chamber device of the invention includes animal cage 10 and transparent chamber 20, which includes first and second compartments 21 and 22 separated by partition plate 23. The compartment 21 has a door and ventilation connection port 26, and the compartments 21 and 22 are provided with communication pipe 29 having opening 29a for introducing ambient air. The device of the invention has ventilation connection port 26 in a side face of the chamber 20, and communication pipe 29 for introducing air on the top face of the chamber 20, so that, with the cage 10 placed in the compartment 21, air flow through the compartment 21 is maintained constantly and allowed to communicate through the cage 10.

5 Claims, 2 Drawing Sheets

CHAMBER DEVICE, RESPIRATORY PHARMACOLOGICAL TEST SYSTEM AND PHARMACOLOGICAL SAFETY TEST METHOD

FIELD OF ART

The present invention relates to a system for respiratory pharmacology test and a chamber device used in the system, which enables respiratory pharmacology test for safety pharmacology studies to be performed on large animals, such as monkeys, dogs, or pigs, under unanesthetized, unrestrained state. The present invention also relates to a method of conducting safety pharmacology studies that allows respiratory, central nervous, and cardiovascular tests for safety pharmacology studies to be conducted all on a large animal of the same species, in particular on the same individual, selected from monkeys, dogs, or pigs.

BACKGROUND ART

In drug development, physiological effects of a test substance have conventionally been assessed using anesthetized, restrained animals. Tests under such conditions, however, are under severe impact of stress and anesthesia, and hard to allow precise evaluation of the effects of a test substance.

Recent safety pharmacology studies for drug development are conducted mostly on unanesthetized, unrestrained test animals under the conditions as stress-free as possible, so as to precisely evaluate the effects of a test substance. The objectives of the safety pharmacology studies are to identify undesirable pharmacodynamic properties of a substance that may have relevance to its human safety; to evaluate adverse pharmacodynamic and/or pathophysiological effects of a substance observed in toxicology and/or clinical studies; and to investigate the mechanism of adverse pharmacodynamic effects observed and/or suspected. Currently, tests on the respiratory, central nervous, and cardiovascular systems are mandatory.

In the respiratory test, parameters such as respiratory rate and respiratory function after administration of a test substance are evaluated for properly assessing the effects of the test substance on the respiratory system. In the central nervous test, motor activity, behavioral changes, coordination, sensory/motor reflex responses, body temperature, and the like after administration of a test substance, are monitored for assessing the effects of the test substance on the respiratory system. In the cardiovascular test, blood pressure, heart rate, electrocardiogram, and the like after administration of a test substance, are evaluated for assessing the effects of the test substance on the cardiovascular system.

Before conducting the respiratory, central nervous, and cardiovascular tests, test animals are often acclimatized to the environment for mitigating stress and other purposes.

However, animals having a higher level of intelligence, such as monkeys, dogs, and pigs, sometimes experience difficulties in acclimatization, depending on the test contents. In particular, the respiratory test has to be conducted with the test animal being housed in a closed transparent chamber that substantially prevents contact with ambient air, such as the one disclosed in Patent Publication 1. In that case, the intelligent animals cannot be acclimatized practically, so that small animals that may easily be acclimatized, have to be used, such as mice, rats, and guinea pigs.

For collecting results as closely simulating the assessment for human as possible, it is ideal to conduct all the safety pharmacology studies of a test substance on the same species, in particular on the same individual of animals that are more closely related to human, such as monkeys, dogs, and pigs. However, under the present circumstances, at least the respiratory test has to be conducted on small animals, and is not conducted on a large animal of the same individual as used in the other tests.

In the test and evaluation using small animals, the difference in physiological functions between the small animals and human may sometimes result in production of metabolites that are different from those produced in human. In that case, it is necessary to freshly conduct a test for human metabolites, which delays drug development. Further, various assessment instrument has been developed for the respiratory, central nervous, and cardiovascular tests, but no chamber device has ever been proposed that allows the respiratory test to be conducted on a large animal, such as monkeys, dogs, or pigs, in particular the same individual as used in the other tests, under unanesthetized, unrestrained state, and that allows acclimatization of such animal therein.

Patent Publication 1: U.S. Patent Application Publication No. 2004/254489.

SUMMARY OF THE INVENTION

It is an object of the present invention to provide a system for respiratory pharmacology test and a chamber device for use in the system, that enables respiratory pharmacology test on an animal selected from monkeys, dogs, or pigs, with easy acclimatization and reduced effect of stress, under unanesthetized, unrestrained state.

It is another object of the present invention to provide a method of conducting safety pharmacology studies that allows the respiratory, central nervous, and cardiovascular tests to be conducted all on the same individual animal selected from monkeys, dogs, or pigs, under unanesthetized, unrestrained state.

According to the present invention, there is provided a chamber device for housing an animal selected from monkeys, dogs, or pigs, for conducting respiratory pharmacology test under unanesthetized, unrestrained state, said chamber device comprising:

an animal cage securing a living space for said animal, said cage having at least front and top faces made of metal grids for allowing inside observation and ventilation, and a grid door in the front face for entrance and exit of said animal, and a transparent chamber, wherein said chamber comprises:

a partition plate for partitioning interior of said chamber into a first compartment for accommodating said cage, and a second compartment for compensating for an effect of atmospheric pressure variations on results of the respiratory test, a door for allowing said cage to be placed in or removed from said first compartment, a ventilation connection port for connecting ventilation means for ventilating said first compartment, a communication pipe having at least three openings, said communication pipe allowing introduction of ambient air into said first compartment and communication between said first and second compartments, wherein said ventilation connection port is arranged at a position in a side face of said chamber and said communication pipe is disposed at a position on a top face of said chamber so that, with said cage placed in said first compartment without an animal therein, air flow through said first compartment is maintained constantly and allowed to communicate through said cage placed in said first compartment.

The animal cage may be a metal cage usually used for raising monkeys, dogs, pigs, or the like for pharmacology tests. The cage is not particularly limited as long as the cage has at least the front and top faces made of metal grids for allowing inside observation and ventilation, a grid door in the front face for entrance and exit of the animal, and a living space for the animal. The cage may preferably be covered with metal walls on its faces other than the front and top faces for blocking view and air flow, in order to narrow the field of view of the animal looking around to reduce source of stress, and to facilitate air flow control through the first compartment, when the cage is placed in the first compartment of the chamber. On the other hand, views through the front and top faces of the cage need to be secured sufficiently for monitoring activities of the animal inside during the respiratory test.

The animal cage may be provided with caster wheels on its lower face at four corners for facilitating transfer of the cage. The cage may also be provided with known restraining means for temporarily restraining the animal upon administration of a test substance for the pharmacology test to the animal.

The chamber may preferably be entirely transparent for allowing inside observation, and may be made of, for example, a known transparent resin. The first compartment of the chamber has to have a sufficient size for the animal cage to be accommodated.

The ventilation connection port in the first compartment and the communication pipe for allowing introduction of ambient air into the first compartment may be arranged suitably at positions in a side face and the top face of the chamber, respectively, so that, with the cage placed in the first compartment without an animal therein, the air flow through the first compartment is maintained constantly and allowed to communicate also through the cage in the first compartment. For example, when the cage has the front and top faces made of ventilating metal grids and the other faces covered with metal walls for blocking view and air flow, the ventilation connection port may be arranged in a side face of the chamber, at a position above half the height of the side face, closer to the front face of the chamber, whereas the communication pipe may be disposed on the top face of the chamber, crossing over the partition plate, for connecting the first and second compartments. It is preferred to arrange the communication pipe at a position generally equidistant from the two side faces of the chamber, crossing over the partition plate at the middle.

The communication pipe has at least three openings, i.e., an opening for connecting to the first compartment, an opening for connecting to the second compartment, and an opening for connecting to the ambient air, so that the atmospheric pressure in the first and second compartments are generally the same.

The partition plate for partitioning the interior of the chamber into the first and second compartments is not particularly limited as long as the plate is capable of blocking the air flow between the first and second compartments. The partitioning plate may usually be a plate made of a transparent resin.

The second compartment provides a space necessary for compensating for an effect, if any, of the atmospheric pressure variations on the results of the respiratory test. The second compartment is partitioned so as not to contact with the air in the first compartment or with the ambient air, other than through the communication pipe having at least three openings for allowing the air in the first and second compartments to contact with the ambient air.

When the animal cage is provided with caster wheels, the cage may shake and easily displaced due to the activities of the animal in the cage placed in the first compartment. Such displacement of the cage varies the air flow in the first compartment during the respiratory test, which may adversely affect accurate data collection. The shaking of the cage may also cause stress for the animal. For preventing the displacement of the cage, it is preferred to provide a cushioning member on the bottom of the first compartment, which has dents for fixing the caster wheels, and a cushioning material for contact with part of the lower face of the cage to fix the entire cage.

According to the present invention, there is also provided a system for respiratory pharmacology test comprising:

the chamber device mentioned above, in which measuring instrument for the respiratory test is fixed at a desired position, and ventilation means is connected to said ventilation connection port, and a transducer for detecting respiratory-waveform signals installed outside said chamber, wherein said transducer measures inner pressure in the first and second compartments, and transmits data to said measuring instrument after compensating for an effect of atmospheric pressure variations in the first compartment on results of respiratory test with inner pressure variations in the second compartment.

The measuring instrument for respiratory test may be a known respiratory-function-measuring device without an animal chamber, which may evaluate, for example, inspiratory time, expiratory time, peak inspiratory flow, peak expiratory flow, tidal volume, expiratory time constant, minute volume, minute respiratory rate, end inspiratory pause, end expiratory pause, enhanced pause, and the like, by downloading into a computer and analyzing respiratory-waveform signals from the transducer for detecting respiratory-waveform signals installed outside the chamber.

According to the present invention, there is also provided a method of conducting safety pharmacology studies comprising the steps of:

(A) providing the system for respiratory pharmacology test discussed above, (B) acclimatizing an animal selected from monkeys, dogs, or pigs, in the animal cage accommodated in the first compartment of the chamber, (C) administering to the acclimatized animal a test substance for safety pharmacology studies, (D) conducting a respiratory test on the animal in the cage administered with the test substance, in unanesthetized, unrestrained state, with the door of the chamber closed, and (E) conducting at least central nervous and cardiovascular tests for safety pharmacology studies of the test substance on the same individual animal as used in the respiratory test.

The system for respiratory pharmacology test and the chamber device for this system according to the present invention employ a transparent chamber of which interior is partitioned into two. In one of the two compartments, a particular animal cage capable of raising there in an animal selected from monkeys, dogs, or pigs, is accommodated, whereas in the other, space is secured for compensating for an effect of atmospheric pressure variations on the results of the respiratory test. A ventilation connection port and a communication pipe for air introduction are provided at predetermined positions in side and top faces, respectively, of the chamber so as to maintain the air flow constantly through the compartment accommodating the animal cage and to allow the air to communicate through the cage accommodated therein. With such constitutions of the present invention, even monkeys, dogs, or pigs may be acclimatized easily, and even when the animal cage is placed in the chamber, the air flow through the compartment, without the animal therein, may be maintained constantly. Thus, a respiratory pharmacology test may be conducted on monkeys, dogs, or pigs in unanesthetized, unrestrained state, which was conventionally impossible.

The method of conducting safety pharmacology studies according to the present invention employs the system for respiratory pharmacology test of the present invention, so that the respiratory test for safety pharmacology studies may be conducted on an animal selected from monkeys, dogs, or pigs, which was conventionally impossible. Since all of the respiratory, central nervous, and cardiovascular tests for safety pharmacology studies may be conducted on such animals, reliable results may be obtained from the same individual, which is extremely useful in drug development.

PREFERRED EMBODIMENTS OF THE INVENTION

The present invention will now be explained in more detail with reference to the drawings, which are not intended to limit the present invention.

Figure 1:
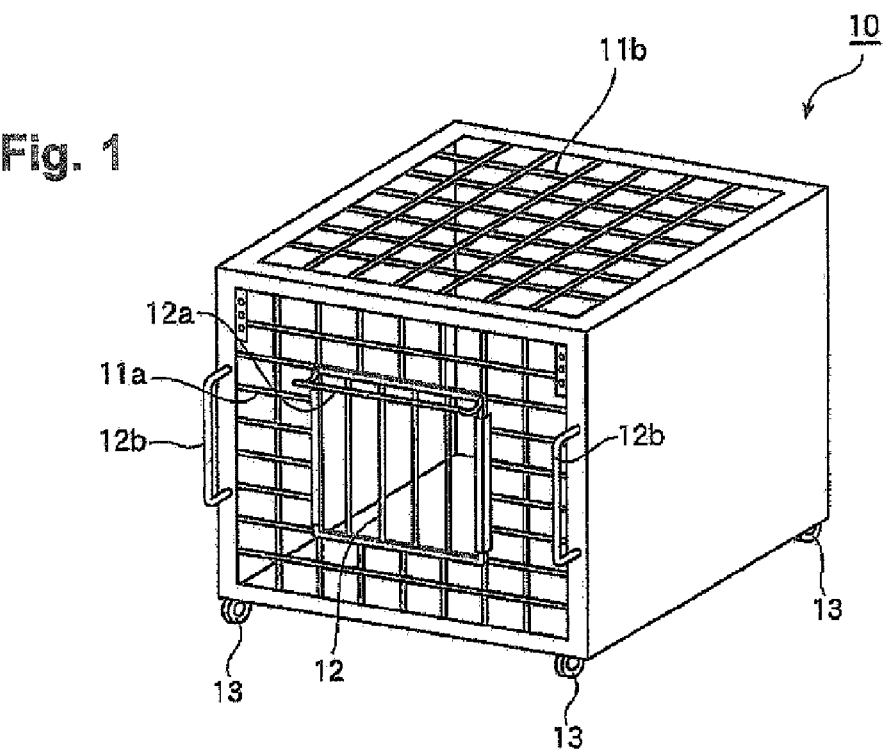
FIG. 1 is a schematic perspective view of an animal cage for use in the chamber device according to the present invention.

FIG. 1 is a schematic perspective view of animal cage 10 for housing an animal selected from monkeys, dogs, or pigs.

The cage 10 secures a living space for the animal, and has the front and top faces made of metal grids 11a and 11b that allow inside observation and ventilation, and the other faces covered with metal walls. Grid door 12 is provided in the front face for allowing entrance and exit of the animal, and has handle 12a for moving the grid door 12 up and down.

Also in the front face, restraining handles 12b are provided, which may be drawn for temporarily restraining the animal in the cage. A restraining mechanism provided in a known animal cage may be used, so that the details are not shown in the drawings.

On the lower face of the cage 10, caster wheels 13 are provided at four corners for facilitating transfer of the cage 10.

Figure 2:
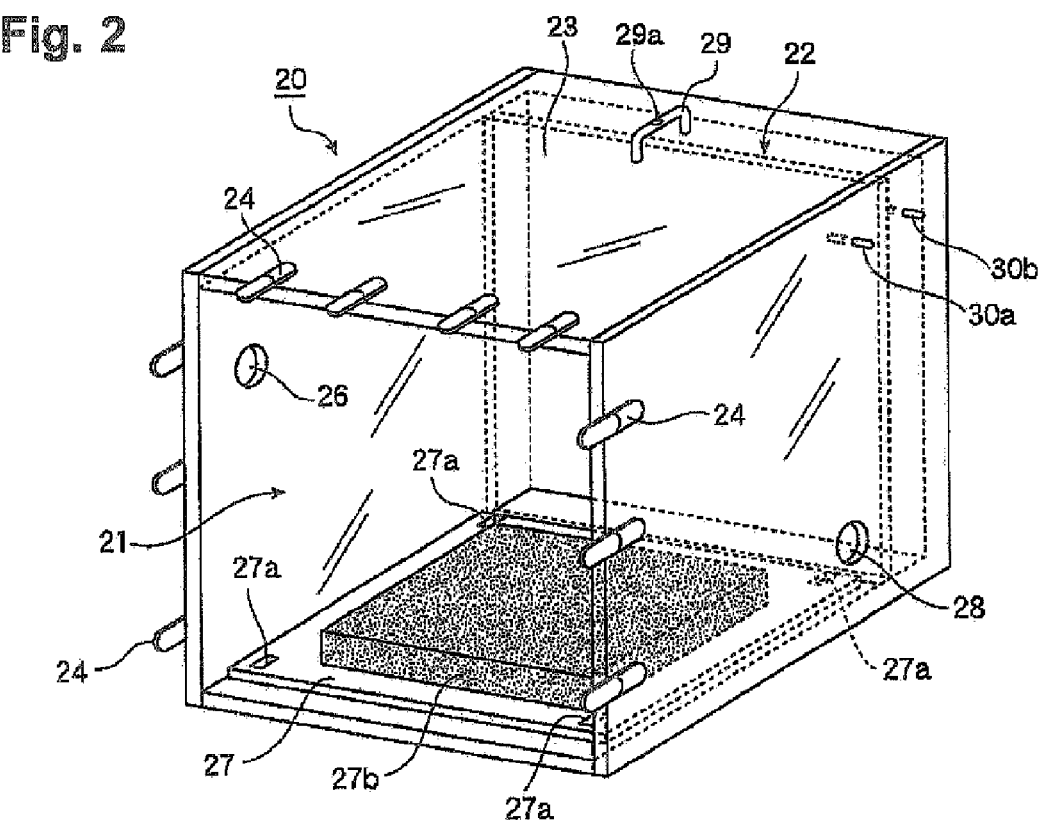
FIG. 2 is a schematic perspective view of a transparent chamber for use in the chamber device according to the present invention, with its door removed.

FIG. 2 is a schematic perspective view for illustrating transparent chamber 20 made of an acrylic resin for accommodating the cage 10 of FIG. 1, with the front door removed.

The chamber 20 has first compartment 21 for accommodating the cage 10 and second compartment 22 for compensating for an effect of atmospheric pressure variations on the results of the respiratory test. The first and second compartments 21 and 22 are separated by transparent partition plate 23.

On the front side of the first compartment 21, door securing hooks 24 are disposed as illustrated for detachably securing a door (not shown), which allows placement or removal of the cage 10.

In a side face of the first compartment, closer to its front side, at a position about three fourths the height from the bottom, ventilation connection port 26 is provided for connecting ventilation means (not shown) for ventilating the first compartment 21.

On the bottom of the first compartment 21, a cushioning member 27 for fixing the cage 10 is disposed. The cushioning member 27 has slots 27a for receiving the caster wheels 13 of the cage 10 fitted therein, and cushion 27b to be in contact with the lower face of the cage 10 to buffer the shaking of the cage 10. The first compartment 21 is also provided with insertion aperture 28, into which a water supply tube (not shown) is to be inserted for supplying drinking water to the animal.

Communication pipe 29 made of a resin is provided, crossing over the partition plate 23, on the top faces of the first and second compartments 21 and 22 at the middle in the rear part of the chamber as illustrated, for allowing contact of the air in the respective compartments and the ambient air. The communication pipe 29 has three openings, namely, one in the portion inserted into the first compartment 21, another in the portion inserted into the second compartment 22, and opening 29a at a position in contact with the ambient air. The animal cage 10 shown in FIG. 1 is placed in the first compartment 21, the door of the first compartment is closed, and ventilation means is connected to the ventilation connection port 26. By applying suction to the first compartment by the ventilation means, ambient air is introduced into the first compartment 21 through the opening 29a of the communication pipe 29.

Through side faces of the first and second compartments 21 and 22 on either side of the partition plate 23, terminals 30a and 30b are provided for connecting a transducer (not shown) for detecting respiratory-waveform signals, which measures the inner pressure of the first and second compartments, and transmits data to measuring instrument (not shown) for respiratory pharmacology test after compensating for the effect of atmospheric pressure variations in the first compartment on the results of the respiratory test with the inner pressure variations in the second compartment.

Figure 3:
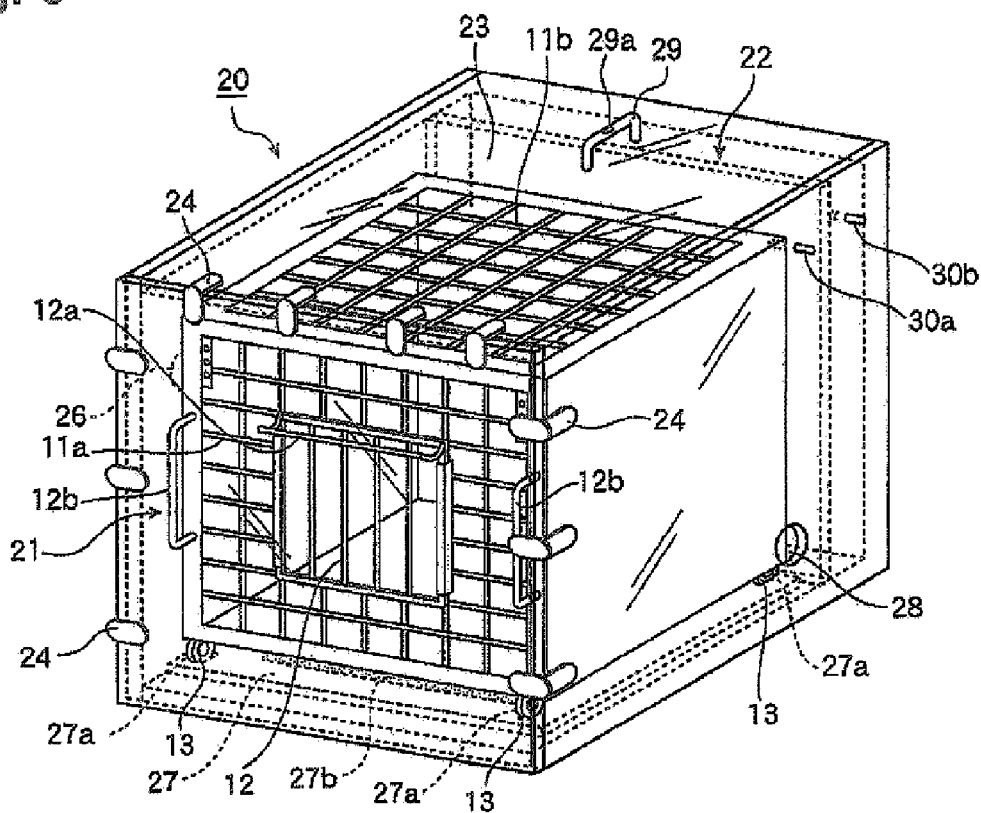
FIG. 3 is a schematic perspective view of the chamber of FIG. 2 and the animal cage of FIG. 1 accommodated therein, with the door of the chamber closed.

The chamber device of the present invention may be assembled, as shown in FIG. 3, by fixing the animal cage 10 of FIG. 1 in the first compartment 21 of the chamber 20 of FIG. 2, and attaching the transparent resin door to the chamber with the door securing hooks 24. In FIG. 3, the same reference numerals refer to the same members as in FIGS. 1 and 2, so that further description is not to be made.

The respiratory pharmacology test may be conducted using the chamber device of the present invention in the following manner. Ventilation means is connected to the ventilation connection port 26 of the chamber 20, and a water supply tube is connected to the insertion aperture 28. The transducer for detecting respiratory-waveform signals is connected to the terminals 30a and 30b, which transducer measures the inner pressure of the first and second compartments, and transmits data to measuring instrument for respiratory pharmacology test after compensating for the effect of atmospheric pressure variations in the first compartment 21 on the results of the respiratory test with the inner pressure variations in the second compartment 22.

Next, the animal cage 10 is fixed at the predetermined position in the first compartment 21 as discussed above, and the animal subject is acclimatized in the cage 10. Then the door of the chamber 20 is secured with the hooks 24, and the measurement may be started in the state as shown in FIG. 3, wherein the ventilation means, the water supply tube, and the measuring instrument for respiratory pharmacology test are omitted.

The measurement may be made while the animal is monitored with a video camera. Known apparatus may be used for conducting the respiratory pharmacology test.

The method of conducting safety pharmacology studies according to the present invention may be carried out on the same individual animal in the animal cage 10, using known apparatus for central nervous test and for cardiovascular test, in addition to the respiratory test discussed above.

The measuring instrument of the apparatus for central nervous test and for cardiovascular test may be installed by firmly fixing the instrument, for example, on part of the metal grid 11b of the top face of the animal cage 10 so as not to be detached by the animal.

What is claimed is:

1. A system for respiratory pharmacology test comprising:
   a chamber device for housing an animal selected from monkeys, dogs, or pigs, for conducting respiratory pharmacology test under unanaesthetized, unrestrained state, said chamber device comprising:
   an animal cage securing a living space for said animal, said cage having at least front and top faces made of metal grids for allowing inside observation and ventilation, and a grid door in the front face for entrance and exit of said animal, and a transparent chamber,
   wherein said chamber comprises:
   a partition plate for partitioning interior of said chamber into a first compartment for accommodating said cage and a second compartment for compensating for an effect of atmospheric pressure variations on results of the respiratory test,
   a door for allowing said cage to be placed in and removed from said first compartment,
   a ventilation connection port for connecting ventilation means for ventilating said first compartment,
   a communication pipe having at least three openings, said communication pipe allowing introduction of ambient air into said first compartment and communication between said first and second compartments, wherein said ventilation connection port is arranged at a position in a side face of said chamber and said communication pipe is disposed at a position on a top face of said chamber so that, with said cage placed in said first compartment without an animal therein, air flow through said first compartment is maintained constantly and allowed to communicate through said cage placed in said first compartment;
   in which a measuring instrument for respiratory test is fixed at a desired position, and ventilation means is connected to said ventilation connection port, and
   a transducer for detecting respiratory-waveform signals installed outside said chamber, wherein said transducer measures inner pressure in the first and second compartments, and transmits data to said measuring instrument after compensating for an effect of atmospheric pressure variations in the first compartment on results of respiratory test with inner pressure variations in the second compartment.

2. The system for respiratory pharmacology test according to claim 1, wherein said cage has caster wheels for facilitating transfer thereof, and wherein said chamber is provided with a cushioning member on the bottom of said first compartment for fixing the caster wheels and buffering shaking of the cage, when the cage is in the first compartment.

3. The system for respiratory pharmacology test according to claim 1, wherein said chamber has, in the first compartment, an insertion aperture for a water supply tube for supplying drinking water to the animal.

4. The system for respiratory pharmacology test according to claim 1, wherein said animal cage is covered with metal walls on faces other than the front and top faces for blocking view and air flow, wherein said ventilation connection port is arranged in a side face of the chamber, at a position above half the height of the side face, closer to the front face of the chamber, and wherein said communication pipe is disposed on the top face of the chamber, crossing over the partition plate, so as to connect the first and second compartments.

5. A method of conducting safety pharmacology studies comprising the steps of:
   (A) providing the system according to claim 1,
   (B) acclimatizing an animal selected from monkeys, dogs, or pigs, in the animal cage accommodated in the first compartment of the chamber,
   (C) administering to the acclimatized animal a test substance for safety pharmacology studies,
   (D) conducting respiratory test on the animal in the cage administered with the test substance, in unanesthetized, unrestrained state, with the door of the chamber closed, and
   (E) conducting at least central nervous and cardiovascular tests for safety pharmacology studies of the test substance on the same individual animal as used in the respiratory test.

* * * * *